United States Patent
Baur et al.

(10) Patent No.: US 8,815,912 B2
(45) Date of Patent: *Aug. 26, 2014

(54) WOUND AND MUCOSA ANTISEPTIC BASED ON BISPYRIDINIUMALKANES

(75) Inventors: Boris Baur, Hamburg (DE); Sabine Behrends, Appen (DE); Jörg Siebert, Norderstedt (DE); Andreas Dettmann, Hamburg (DE); Mona Golombiewski, Lüneburg (DE)

(73) Assignee: L'Air Liquide Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 132 days.

This patent is subject to a terminal disclaimer.

(21) Appl. No.: 12/904,424

(22) Filed: Oct. 14, 2010

(65) Prior Publication Data

US 2011/0092543 A1 Apr. 21, 2011

Related U.S. Application Data

(60) Provisional application No. 61/251,941, filed on Oct. 15, 2009.

(30) Foreign Application Priority Data

Oct. 15, 2009 (DE) .......................... 10 2009 049 504

(51) Int. Cl.
*A01N 43/40* (2006.01)
*A61K 31/44* (2006.01)
*A61K 9/00* (2006.01)
*A61K 9/08* (2006.01)
*A61K 47/10* (2006.01)

(52) U.S. Cl.
CPC ................. *A61K 9/0014* (2013.01); *A61K 9/08* (2013.01); *A61K 31/44* (2013.01); *A61K 47/10* (2013.01)
USPC ........................................................ 514/332

(58) Field of Classification Search
None
See application file for complete search history.

(56) References Cited

U.S. PATENT DOCUMENTS

| | | | |
|---|---|---|---|
| 8,541,454 B2 * | 9/2013 | Dettman et al. | 514/332 |
| 2005/0119313 A1 | 6/2005 | Behrends et al. | |
| 2006/0159647 A1 * | 7/2006 | Beilfuss et al. | 424/70.13 |
| 2006/0165612 A1 * | 7/2006 | Beilfuss et al. | 424/49 |
| 2007/0253991 A1 * | 11/2007 | Glick et al. | 424/405 |
| 2008/0221165 A1 * | 9/2008 | Siebert et al. | 514/332 |
| 2008/0254084 A1 | 10/2008 | Behrends et al. | |
| 2009/0076084 A1 | 3/2009 | Krug et al. | |
| 2009/0311200 A1 * | 12/2009 | Lambert et al. | 424/52 |
| 2011/0217360 A1 | 9/2011 | Aydinoglu | |

FOREIGN PATENT DOCUMENTS

| | | |
|---|---|---|
| DE | 27 08 331 | 9/1977 |
| DE | 19647692 | 6/1998 |
| DE | 10205883 | 8/2003 |
| DE | 102005058978 | 3/2007 |
| DE | 102005063375 | 4/2007 |
| DE | 102008011692 | 9/2009 |
| EP | 0411315 | 2/1991 |
| EP | 1982696 | 10/2008 |
| GB | 1 533 952 | 11/1978 |
| WO | 9820095 | 5/1998 |
| WO | 2009106468 | 9/2009 |
| WO | WO 2010 055122 | 5/2010 |

OTHER PUBLICATIONS

Schülke & Mayr, Schnelle Wundheilung. Ihre Patienten sagen Danke! Octeniver—Wundgel und Wundspüllösung für Tiere [Rapid would healing—Its patients say thank you! Octeniver—Would gel and would rinse solution for animals]. Norderstedt, 2008 (2065/I/08. 08).—Compnay brochure.
Schülke & Mayr: Präparate-Information Wundbehandlung. Octenilin® Wundspüllösung [Preparations-information would treatment. Octenilin® would rinse solution]. Norderstedt, 2009 (2288/I/09.09). Company brochure.
First Office Action for DE Application No. 10 2009 049 504.5-41 and English translation.

* cited by examiner

*Primary Examiner* — James D Anderson
*Assistant Examiner* — William Lee
(74) *Attorney, Agent, or Firm* — Allen E. White

(57) ABSTRACT

The invention relates to an antimicrobially effective composition which comprises a) 0.001 to 1% by weight of bispyridiniumalkane, b) humectant and c) water. The composition has an osmolality of from 230 to 350 mOsmol/kg and is free from surfactant. It is used as wound and mucosa antiseptic.

1 Claim, No Drawings

WOUND AND MUCOSA ANTISEPTIC BASED ON BISPYRIDINIUMALKANES

CROSS-REFERENCE TO RELATED APPLICATIONS

This application claims the benefit of U.S. Provisional Application No. 61/251,941, filed Oct. 15, 2009 and German Application No. 10 2009 049504.5 filed Oct. 15, 2009, the entire contents of which are incorporated herein by reference.

FIELD OF INVENTION

The present invention relates to an antimicrobially effective composition based on bispyridiniumalkanes such as octenidine dihydrochloride and also to the use of the composition as wound and mucosa antiseptic.

BACKGROUND

Wound and mucosa antiseptics based on bispyridiniumalkanes are known. Bispyridiniumalkanes are active ingredients which are characterized by high efficacy coupled with low absorption on wounds. For example, EP 0 411 315 A1 discloses an aqueous antiseptic composition which comprises octenidine dihydrochloride and phenoxyethanol and/or phenoxy-propanol in a specific weight ratio. Octenidine dihydrochloride (referred to as octenidine below) is a quaternary ammonium compound, and specifically a bispyridiniumalkane, with the following structure:

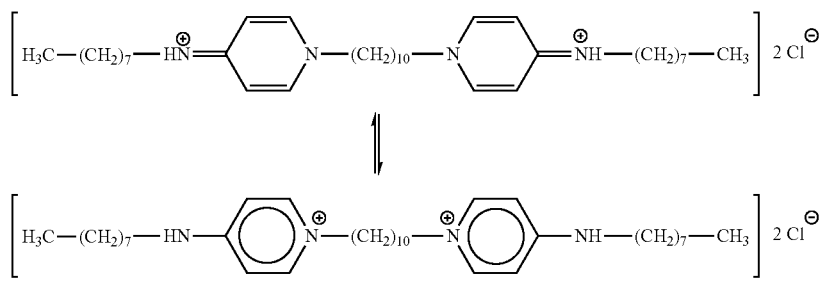

The compositions according to DE 196 47 692 A1 comprise octenidine, $C_1$- to $C_8$-alkyl alcohol, nonionic and/or cationic surfactant and skin-compatible α-hydroxycarboxylic acid and are used as washing hand disinfectant.

Moreover, the product Octenisept® has been successfully sold for many years as mucosa and wound antiseptic.

Octenisept® consists inter alia of 0.1% by weight of octenidine dihydrochloride, 2% by weight of phenoxyethanol and cocamidopropylbetaine as amphoteric surfactant in aqueous solution.

EP 1 982 696 A1 discloses antiseptic gels based on a specific poloxamer. Poloxamers are nonionic surfactants and are prepared by copolymerizing propylene oxide with ethylene oxide. The gels comprise octenidine and/or polyhexanide as active ingredient and are characterized by an increase in the viscosity in the range from 20 to 30° C.

The aqueous antiseptic according to DE 102 05 883 A1 comprises octenidine and nonionic surfactant selected from alcohol polyalkoxylates, polysorbates and alkyl glycosides. It is free from alcohols and can be both rendered isotonic and also diluted with salt solutions to give isotonic solutions without resulting in precipitations. As explained in DE 102 05 883 A1, precipitations in an antiseptic that has been rendered isotonic are undesired because they lead to hypo- or hypertonic solutions or to a change in the active ingredient content.

The known wound and mucosa antiseptics are associated with disadvantages.

Antiseptics which necessarily require the presence of alcohols (for example aliphatic alcohols such as ethanol, propanol or butanol or aromatic alcohols such as benzyl alcohol, phenoxyethanol or phenoxypropanol) should be avoided on account of potential allergic reactions.

Antiseptics with a content of (cationic, anionic, nonionic and/or amphoteric) surfactant as secondary constituent likewise involve the risk of an allergy potential and can lead to severe undesired foaming for example in the case of ultrasound assisted wound treatment (UAW).

Moreover, compositions for wound and mucosa antisepsis should be able to be formulated isotonically, as is already described in DE 102 05 883 A1. Solutions isotonic to blood plasma contain dissolved particles in a concentration of 290 mOsmol/kg, e.g. 0.9% aqueous NaCl solution. The isotonicity of antiseptics is usually adjusted using inorganic salts, as are present in Ringer's solutions and NaCl solution. However, in the case of antiseptics which are rendered isotonic with the help of inorganic salts such as NaCl or Ringer's solution, there is always the risk of precipitations during storage, especially at a low temperature.

Ultimately, antiseptics are undesired which comprise large amounts of active ingredient and/or two or more active ingredients for satisfactory antimicrobial efficacy, or which comprise one or more secondary constituents since this is associated with the risk that the composition could not be used in patients who cannot tolerate just one of the active ingredients or secondary constituents. Consequently, antiseptics should only comprise the ingredients that are absolutely necessary for the application.

The object of the present invention was therefore to provide a composition for use as wound and mucosa antiseptic. The composition does not automatically require the presence of surfactant for good wettability, of alcohol for good efficacy and/or of inorganic salts for isotonicity. The compositions should be stable over a broad temperature range, i.e. not have a tendency towards separation of constituents (for example precipitations).

SUMMARY OF THE INVENTION

It has now surprisingly been found that a composition for use as wound and mucosa antiseptic is achieved by an antimicrobially effective composition which comprises a) 0.001 to 1% by weight of bispyridiniumalkane, b) humectant and c) water.

DETAILED DESCRIPTION OF THE INVENTION

The composition according to the invention has (i) an osmolality of from 230 to 350 mOsmol/kg. Since the osmotic pressure in a solution behaves proportionally to the depression in the freezing point of a solution, the osmolality can be determined in accordance with the principle of freezing point depression. This determination can be carried out, for example, using a semimicro osmometer from Knauer.

In addition, the composition is (ii) free from surfactant. The obligatorily prescribed bispyridiniumalkane of component a) is not considered to be a surfactant for the purposes of the description of the present invention. "Surfactant-free" thus means that the composition according to the invention comprises no anionic, cationic, nonionic or amphoteric surfactant besides the one or, if appropriate, more bispyridiniumalkanes. In a particularly preferred embodiment, no anionic, cationic, nonionic or amphoteric surfactant—apart from octenidine—is present in the composition according to the invention.

The invention is based inter alia on the fact that it has been found that the composition has an adequate efficacy for wound and mucosa antisepsis even in the absence of (aliphatic and aromatic) alcohols. Through the physiological pH, the isotonicity, the octenidine that is classed as toxicologically acceptable as active ingredient and the omission of surfactants and further substances that are not necessarily required for antimicrobial effectiveness, it is possible to provide a well tolerated formulation which is stable in all climatic zones and which, moreover, can be sterilized. A further surprising effect is the adjustment of the blood isotonicity with the multifunctional raw material glycerol, which is additionally also an excellent moisturizing factor. The moisturization of a wound is essential for good wound healing. As a result, it is possible to dispense with the addition of inorganic salts for adjusting the isotonicity, as are present, for example, in isotonic sodium chloride solution and Ringer's solution. This ensures firstly very good tolerability and secondly improved stability since an addition of inorganic salts, in particular in combination with octenidine, can lead to the formation of crystalline precipitates.

For example, it was surprising that the known good efficacy of octenidine is adversely affected by the addition of surfactants such as, for example, cocamidopropylbetaine, as is shown in example 5. An additional benefit of omitting the surfactant consists in significantly better tolerability.

A particularly preferred composition according to the invention is (iii) free from alcohol. Thus, in particular the presence of aliphatic alcohols such as ethanol, propanol or butanol, and aromatic alcohols such as benzyl alcohol, phenoxyethanol or phenoxypropanol, as are present in numerous antiseptics according to the prior art, is excluded.

In addition, a preferred composition according to the invention is (iv) free from inorganic salts, for example those salts which are customary for the formulation of isotonic compositions (Ringer's solutions, sodium chloride solutions).

The osmolality of the composition according to the invention is preferably 250 to 330 mOsmol/kg, preferably 260 to 320 mOsmol/kg, in particular 270 to 310 mOsmol/kg.

a) Bispyridiniumalkane

The term bispyridiniumalkane includes the bis[4-(substituted-amino)-1-pyridinium]alkanes, disclosed in DE 27 08 331 C2, of the general formulae (I) or (II)

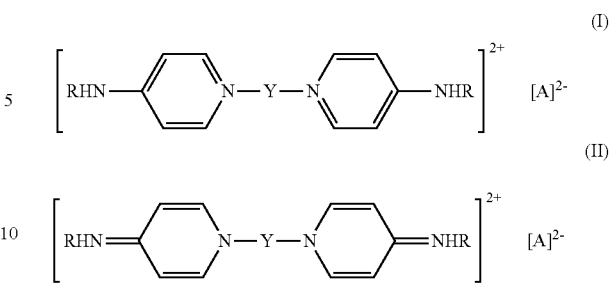

in which
Y is an alkylene group having 4 to 18 carbon atoms,
R is an alkyl group having 6 to 18 carbon atoms or a cycloalkyl group having 5 to 7 carbon atoms or the phenyl radical, which is substituted by a halogen atom, and
A is one or more anions.

Strictly speaking, the aforementioned definition of A applies for mono- and divalent anions, although A can of course also be a polyvalent anion, e.g. phosphate or orthosilicate. Furthermore, the term bispyridiniumalkane includes the various prototropes of the compounds of the formula (I), as is disclosed, for example, in DE 196 47 692 A1.

In all embodiments of the invention, however, it is preferred that component a) is octenidine dihydrochloride (R=n-octyl, Y=n-decenyl; A=2×Cl).

Preferred amounts of component a) in the composition according to the invention are 0.01 to 1% by weight, preferably 0.03 to 0.5% by weight, more preferably 0.05 to 0.2% by weight, in particular 0.08 to 0.12% by weight, such as about 0.1% by weight.

b) Humectants

Preferred humectants are selected from the group of polyhydric alcohols and mixtures thereof, preferably glycerol, 1,2-propylene glycol, sorbitol, glucose, fructose, glucuronic acid, lactose, lactic acid, lactates, lactulose, polyethylene glycols, sucrose, hyaluronic acid, xylitol, xylose and mixtures thereof. It is particularly preferred that component b) is glycerol.

Preferred amounts of component b), in particular glycerol, are 1.0 to 4.0% by weight, preferably 1.5 to 3.5% by weight, more preferably 2.0 to 3.0% by weight, in particular 2.2 to 2.6% by weight, such as 2.3 to 2.5% by weight.

Consequently, particular preference is given to a composition which consists of the components
a) octenidine dihydrochloride, preferably in an amount of from 0.05 to 0.2% by weight,
b) glycerol, preferably in an amount of from 2.2 to 2.6% by weight, and
c) water
and has an osmolality of from 270 to 310 mOsmol/kg.

Compositions according to the invention are used as wound and mucosa antiseptic, both for people and also for animals. Examples of animals for which the composition can be used are all vertebrates. The use can also take place in ultrasound assisted wound treatment (UAW).

The advantages of the present invention are evident in particular from the following examples.

EXAMPLES

The percentages below are based on the weight (unless expressly stated otherwise).

Example 1

Surface Tension

To determine the surface tension using the method of the hanging drop, the contact angle measuring instrument DSA 10 from Krüss GmbH, Hamburg, Federal Republic of Germany, was used. In this method, a hanging drop is produced using a hollow needle. The drop contour that is formed is dependent on the surface tension and is transferred to the PC via a video camera. Then, by means of the software, a contour is placed around the drop and the surface tension is calculated from the contour.

A needle with an outer diameter of 1.835 mm was used. The following results were obtained (Table 1):

TABLE 1

| Formulation | Octenidine [%] | Glycerol [%] | Water [%] | Surface tension [mN/m] |
|---|---|---|---|---|
| 1A | 0.1% | 2.42 | 97.48 | 51.7 |
| 1B | — | 2.42 | 97.58 | 72.8 |
| 1C | — | — | 100 | 72.8 |

Accordingly, an aqueous solution containing 0.1% by weight of octenidine exhibits a significantly lower surface tension than an aqueous solution without octenidine.

Example 2

Wetting Effect

As regards the wetting effect, the following were compared:
Octenisept
Ringer's solution
0.1% octenidine in water In this experiment, raw meat was used as a model for wound and mucosa.

To determine the wetting behaviour, in each case the spraying and rinsing method were tested under conditions simulating those met in practice. For this, pieces of raw meat were wetted on the level and on an incline (ca.) 30° and the course of the liquid and the rinsing-off of residual particles on the surface were assessed macroscopically.

Spraying Method:
The raw meat was sprayed until completely wet using a spray pump and the run-off behaviour was assessed.

Rinsing Method:
Using a disposable pipette, ca. 3 ml were applied and the run-off behaviour was assessed.

Result:
Macroscopically, it was not possible to detect any differences in wetting or cleaning behaviour of the various formulations and/or various methods given above.

Evaluation:
An addition of surfactant such as cocamidopropylbetaine, which is present in Octenisept, is thus not necessary for a wound and mucosa antiseptic. Evidently, octenidine dihydrochloride, being a quaternary ammonium compound, adequately reduces the surface tension.

Example 3

Osmolality

For this investigation, aqueous solutions with a content of 0.1% by weight of octenidine with various amounts of glycerol were prepared and their osmolality was investigated. The results are shown below (Table 2). The osmolality was determined using a semimicro osmometer from Knauer.

TABLE 2

| Formulation | Glycerol [%] | Osmolality [mOsmol/kg] |
|---|---|---|
| 3A | 2.0 | 231 |
| 3B | 2.1 | 240 |
| 3C | 2.2 | 261 |
| 3D | 2.3 | 268 |
| 3E | 2.4 | 287 |
| 3F | 2.5 | 295 |
| 3G | 2.6 | 309 |
| 3H | 2.7 | 317 |
| 3I | 2.8 | 331 |
| 3J | 2.9 | 344 |
| 3K | 3.0 | 351 |

Example 4

Stability

To investigate the stability, aqueous solutions containing 0.1% by weight of octenidine were in each case rendered isotonic (290 mOsmol/kg). The results are shown in Table 3.

TABLE 3

| Octenidine [%] | Adjustment of the isotonicity with | Stability |
|---|---|---|
| 0.10 | 0.85% sodium chloride | Spontaneous formation of crystalline precipitations |
| 0.10 | 99.9% Ringer's solution | Spontaneous formation of crystalline precipitations |
| 0.10 | 2.4% glycerol (99.8% strength) | Stable between +4° C. and +40° C. |

Aqueous solutions with a content of 0.1% by weight of octenidine are accordingly not stable as Ringer's solution and isotonic sodium chloride solution. By contrast, aqueous isotonic octenidine-containing solutions containing glycerol are stable.

Example 5

Efficacy when Adding Other Compounds

In a quantitative suspension test in accordance with DGHM (status: 1 Sep. 2001, Gebel et al.), the efficacy of various formulations was investigated. In each case, aqueous formulations containing 0.1% by weight of octenidine and 1% by weight of the stated surfactant (or 2.42% of glycerol) were tested. The experiments were carried out with and without loading. The fcs loading simulates the organic loadings in the wound.

| | Surfactant | Without loading | | | | | 10% fcs (foetal calf serum) | | | | |
|---|---|---|---|---|---|---|---|---|---|---|---|
| | | 15 sec | 30 sec | 1 min | 2 min | 3 min | 15 sec | 30 sec | 1 min | 2 min | 3 min |
| | | *P. aeruginosa* | | | | | | | | | |
| 1 | — | 5.61 | 5.72 | 5.62 | 5.69 | 5.71 | 5.60 | 5.80 | 5.85 | 5.88 | 5.84 |
| 2 | 2.42% glycerol | 5.61 | 5.72 | 5.62 | 5.69 | 5.71 | 5.90 | 5.80 | 5.85 | 5.88 | 5.84 |
| 3 | Cocamidopropyldimethylamine oxide | 5.61 | 5.72 | 5.62 | 5.69 | 5.71 | 1.83 | 3.58 | 4.90 | 5.88 | 5.84 |

|  | Surfactant | Without loading | | | | | 10% fcs (foetal calf serum) | | | | |
|---|---|---|---|---|---|---|---|---|---|---|---|
|  |  | 15 sec | 30 sec | 1 min | 2 min | 3 min | 15 sec | 30 sec | 1 min | 2 min | 3 min |
| 4 | Macrogol glycerol hydroxystearate 40 EO | 5.61 | 5.72 | 5.62 | 5.69 | 5.71 | 2.07 | 2.69 | 5.85 | 5.88 | 5.84 |
| 5 | Cocamidopropylbetaine | 5.61 | 5.72 | 5.62 | 5.69 | 5.71 | 0.00 | 0.00 | 0.00 | 0.00 | 0.00 |
| 6 | Sodium cocoamphopropionate | 5.61 | 5.72 | 5.62 | 5.69 | 5.71 | 0.00 | 0.00 | 0.00 | 0.00 | 0.00 |
| 7 | Cocamidopropylhydroxysultaine | 1.41 | 2.46 | 4.51 | 5.69 | 5.71 | 0.00 | 0.00 | 0.00 | 0.00 | 0.00 |
| 8 | Sodium cocoamphoacetate | 0.00 | 0.00 | 1.18 | 1.34 | 1.57 | 0.00 | 0.00 | 0.00 | 0.00 | 0.00 |
|  | *S. aureus* | | | | | | | | | | |
| 9 | — | 5.74 | 5.80 | 5.81 | 5.76 | 5.79 | 3.06 | 5.69 | 5.68 | 5.79 | 5.76 |
| 10 | 2.42% glycerol | 5.44 | 5.80 | 5.81 | 5.76 | 5.79 | 3.88 | 5.69 | 5.68 | 5.79 | 5.76 |
| 11 | Cocamidopropyldimethylamine oxide | 3.27 | 5.50 | 5.81 | 5.76 | 5.79 | 2.86 | 4.37 | 5.68 | 5.79 | 5.76 |
| 12 | Macrogol glycerol hydroxystearate 40 EO | 3.72 | 4.72 | 5.51 | 5.76 | 5.79 | 5.76 | 5.69 | 5.68 | 5.79 | 5.76 |
| 13 | Cocamidopropylbetaine | 1.77 | 2.69 | 4.81 | 5.46 | 5.79 | 2.51 | 5.69 | 5.68 | 5.79 | 5.76 |
| 14 | Sodium cocoamphopropionate | 2.12 | 4.31 | 5.81 | 5.76 | 5.79 | 2.12 | 4.61 | 5.68 | 5.79 | 5.76 |
| 15 | Cocamidopropylhydroxysultaine | 2.63 | 3.37 | 4.58 | 4.81 | 5.79 | 2.33 | 4.54 | 5.68 | 5.79 | 5.76 |
| 16 | Sodium cocoamphoacetate | 0.00 | 0.00 | 0.00 | 0.00 | 0.00 | 0.00 | 0.00 | 0.00 | 0.00 | 0.00 |
|  | *C. albicans* | | | | | | | | | | |
| 17 | — | 4.90 | 4.90 | 4.95 | 5.00 | 4.85 | 4.90 | 4.78 | 4.85 | 4.85 | 4.90 |
| 18 | 2.42% glycerol | 4.90 | 4.90 | 4.95 | 5.00 | 4.85 | 4.90 | 4.78 | 4.85 | 4.85 | 4.90 |
| 19 | Cocamidopropyldimethylamine oxide | 0.78 | 0.85 | 0.99 | 1.36 | 1.30 | 0.60 | 0.53 | 0.64 | 0.85 | 1.02 |
| 20 | Macrogol glycerol hydroxystearate 40 EO | 4.12 | 4.90 | 4.95 | 5.00 | 4.85 | 1.43 | 1.57 | 3.31 | 4.85 | 4.90 |
| 21 | Cocamidopropylbetaine | 0.74 | 0.77 | 0.86 | 0.96 | 0.82 | 0.70 | 0.65 | 0.74 | 0.78 | 0.85 |
| 22 | Sodium cocoamphopropionate | 0.56 | 0.61 | 0.83 | 1.03 | 1.04 | 0.57 | 0.70 | 0.77 | 0.81 | 0.88 |
| 23 | Cocamidopropylhydroxysultaine | 0.58 | 0.70 | 0.91 | 0.99 | 0.85 | 0.68 | 0.58 | 0.58 | 0.74 | 0.84 |
| 24 | Sodium cocoamphoacetate | 0.78 | 0.85 | 0.83 | 0.94 | 0.78 | 0.57 | 0.63 | 0.75 | 0.84 | 0.92 |

The results show that in aqueous formulations with a content of octenidine with glycerol, the impairment of the biocidal efficacy observed with various surfactants does not occur. This is established to a yet more marked degree especially in the case of tests with loading.

What is claimed is:

1. An antimicrobially effective composition, wherein the composition consists of a) octenidine dihydrochloride in an amount of from 0.05 to 0.2% by weight, b) glycerol in an amount of from 2.2 to 2.6% by weight, and c) water as remainder, and has an osmolality of from 270 to 310 mOsmol/kg.

* * * * *